US008057811B2

(12) United States Patent
Surman et al.

(10) Patent No.: US 8,057,811 B2
(45) Date of Patent: Nov. 15, 2011

(54) STABLE CLOZAPINE SUSPENSION FORMULATION

(75) Inventors: Peter William Surman, Auckland (NZ); Sharon Ferguson, Auckland (NZ); Wai Bik Mak, Auckland (NZ); Andrew Douglas McLeod, Auckland (NZ)

(73) Assignee: Douglas Pharmaceuticals Limited, Auckland (NZ)

( * ) Notice: Subject to any disclaimer, the term of this patent is extended or adjusted under 35 U.S.C. 154(b) by 1379 days.

(21) Appl. No.: 10/561,930

(22) PCT Filed: Jul. 22, 2004

(86) PCT No.: PCT/NZ2004/000158
§ 371 (c)(1),
(2), (4) Date: May 23, 2006

(87) PCT Pub. No.: WO2005/007168
PCT Pub. Date: Jan. 27, 2005

(65) Prior Publication Data
US 2006/0240050 A1 Oct. 26, 2006

(30) Foreign Application Priority Data
Jul. 23, 2003 (NZ) ........................................ 527142

(51) Int. Cl.
*A61K 9/00* (2006.01)
(52) U.S. Cl. ..................................................... 424/400
(58) Field of Classification Search .................... 424/400
See application file for complete search history.

(56) References Cited

U.S. PATENT DOCUMENTS

| | | | |
|---|---|---|---|
| 4,310,524 A | 1/1982 | Wiech et al. | |
| 4,425,346 A * | 1/1984 | Horlington | 514/249 |
| 5,221,679 A | 6/1993 | Meltzer | |
| 5,223,399 A | 6/1993 | Lieberman et al. | |
| 5,312,819 A | 5/1994 | Fischer et al. | |
| 5,521,222 A * | 5/1996 | Ali et al. | 514/772.6 |
| 5,563,134 A | 10/1996 | Fischer et al. | |
| 5,744,468 A | 4/1998 | Lin et al. | |
| 5,827,819 A | 10/1998 | Yatvin et al. | |
| 5,869,479 A | 2/1999 | Kreutner et al. | |
| 5,871,778 A | 2/1999 | Kino et al. | |
| 5,922,341 A | 7/1999 | Smith et al. | |
| 5,955,459 A | 9/1999 | Bradley et al. | |
| 5,972,389 A | 10/1999 | Shell et al. | |
| 5,994,384 A | 11/1999 | Akerman et al. | |
| 6,024,977 A | 2/2000 | Yatvin et al. | |
| 6,100,256 A | 8/2000 | Baker et al. | |
| 6,103,735 A | 8/2000 | Aslanian et al. | |
| 6,147,072 A | 11/2000 | Bymaster et al. | |
| 6,150,353 A | 11/2000 | Brockkamp et al. | |
| 6,166,008 A | 12/2000 | Johnson et al. | |
| 6,174,886 B1 | 1/2001 | Pineiro et al. | |
| 6,197,764 B1 | 3/2001 | Bradley et al. | |
| 6,210,712 B1 | 4/2001 | Edgren et al. | |
| 6,228,864 B1 | 5/2001 | Smith et al. | |
| 6,228,875 B1 | 5/2001 | Tsai et al. | |
| 6,231,594 B1 | 5/2001 | Dae | |
| 6,300,332 B1 | 10/2001 | Chang et al. | |
| 6,309,669 B1 | 10/2001 | Setterstrom et al. | |
| 6,331,536 B1 | 12/2001 | Radulovacki et al. | |
| 6,350,773 B1 | 2/2002 | Marquis | |
| 6,358,944 B1 | 3/2002 | Lederman et al. | |
| 6,372,919 B1 | 4/2002 | Lippa et al. | |
| 6,375,944 B1 | 4/2002 | Trinchieri et al. | |
| 6,380,223 B1 | 4/2002 | Dow et al. | |
| 6,383,471 B1 | 5/2002 | Chen et al. | |
| 6,384,077 B1 | 5/2002 | Peet et al. | |
| 6,395,727 B1 | 5/2002 | Guadagno et al. | |
| 6,419,952 B2 | 7/2002 | Wong et al. | |
| 6,420,351 B1 | 7/2002 | Tsai et al. | |
| 6,444,665 B1 | 9/2002 | Helton et al. | |
| 6,479,074 B2 | 11/2002 | Murdock et al. | |
| 6,495,154 B1 | 12/2002 | Tam et al. | |
| 6,514,530 B2 | 2/2003 | Skluzacek et al. | |
| 6,566,389 B1 | 5/2003 | Zisapel et al. | |
| 6,569,903 B2 * | 5/2003 | Honma et al. | 514/649 |
| 6,572,880 B2 | 6/2003 | Murdock et al. | |
| 6,572,890 B2 | 6/2003 | Faour et al. | |
| 6,599,532 B2 | 7/2003 | Faour et al. | |
| 6,622,036 B1 | 9/2003 | Suffin | |
| 6,676,931 B2 | 1/2004 | Dugger, III | |
| 6,680,310 B2 | 1/2004 | Belanoff et al. | |
| 6,689,812 B2 | 2/2004 | Peet et al. | |
| 6,699,893 B2 | 3/2004 | Dow et al. | |
| 6,716,416 B2 | 4/2004 | Rabinowitz et al. | |
| 6,727,242 B2 | 4/2004 | Radulovacki et al. | |
| 6,919,330 B2 | 7/2005 | Vaddadi | |
| 6,919,350 B2 | 7/2005 | Chang et al. | |
| 6,929,803 B2 | 8/2005 | Wong et al. | |
| 6,936,601 B2 | 8/2005 | Helton et al. | |
| 6,946,141 B2 | 9/2005 | Tam et al. | |
| 6,964,962 B2 | 11/2005 | Wong et al. | |

(Continued)

FOREIGN PATENT DOCUMENTS

EP 0669128 B1 8/1995

(Continued)

OTHER PUBLICATIONS

Ramuth et al (A liquid clozapine preparation for oral administration in hospital. Pharm J 1996; 257: 190-1).*
Walker et al (Stability of Clozapine Stored in Oral Suspension Vehicles at Room Temperature. Canadian J Hospital Pharmacy. 58:5. (2005).*
Remington (Remington: The Science and Practice of Pharmacy 20th edition (2000).*
European Search Report of Application No. 04 748 853.1-1219 dated Apr. 23, 2009.
Ramuth et al., Pharm Journal 257:190-191, 1996.
Physicians' Desk Reference. 55th ed. Montvale, NJ: Thomson PDR; 2001:2155-2159.
Merck Index. 13th ed. Merck: Whitehouse Station, NJ, 2001; 2448.
Letter from Irish Medicines Board dated Mar. 6, 2009.

* cited by examiner

*Primary Examiner* — Jake M. Vu
(74) *Attorney, Agent, or Firm* — Caesar, Rivise, Bernstein, Cohen & Pokotilow, Ltd.

(57) ABSTRACT

A physicochemically stable aqueous composition including clozapine suspension.

19 Claims, 1 Drawing Sheet

U.S. PATENT DOCUMENTS

| | | | |
|---|---|---|---|
| 6,977,070 B2 | 12/2005 | Dugger, III |
| 6,998,110 B2 | 2/2006 | Dugger, III |
| 7,008,444 B2 | 3/2006 | Dae et al. |
| 7,008,641 B2 | 3/2006 | Faour et al. |
| 7,030,108 B2 | 4/2006 | Richter et al. |
| 7,038,085 B2 | 5/2006 | Rariy et al. |
| 7,045,543 B2 | 5/2006 | Yatvin et al. |
| 7,052,679 B2 | 5/2006 | Rabinowitz et al. |
| 7,078,020 B2 | 7/2006 | Rabinowitz et al. |
| 7,090,830 B2 | 8/2006 | Hale et al. |
| 7,098,229 B2 | 8/2006 | Lippa et al. |
| 7,119,118 B2 | 10/2006 | Peet et al. |
| 7,160,898 B2 | 1/2007 | Radulovacki et al. |
| 7,166,593 B2 | 1/2007 | Dow et al. |
| 7,179,849 B2 | 2/2007 | Terry |
| 7,241,797 B2 | 7/2007 | Horseman |
| 7,414,058 B2 | 8/2008 | Grzelak et al. |
| 7,429,575 B2 | 9/2008 | Yu et al. |
| 7,429,580 B2 | 9/2008 | Gadde et al. |
| 7,489,964 B2 | 2/2009 | Suffin et al. |
| 7,491,715 B2 | 2/2009 | Ek et al. |
| 7,517,871 B2 | 4/2009 | Ek et al. |
| 7,517,900 B2 | 4/2009 | Pendri et al. |
| 7,524,819 B2 | 4/2009 | Shashoua |
| 7,544,681 B2 | 6/2009 | Nudelman et al. |
| 7,550,454 B2 | 6/2009 | Ek et al. |
| 7,569,611 B2 | 8/2009 | Oberegger et al. |
| 7,572,776 B2 | 8/2009 | Yu et al. |
| 7,572,802 B2 | 8/2009 | Boyle et al. |
| 7,598,239 B2 | 10/2009 | Nudelman et al. |
| 7,601,337 B2 | 10/2009 | Rabinowitz et al. |
| 7,601,740 B2 | 10/2009 | Weiner et al. |
| 7,619,006 B2 | 11/2009 | Nudelman et al. |
| 7,629,342 B2 | 12/2009 | Ewing et al. |
| 7,645,750 B2 | 1/2010 | Wu |
| 2001/0029257 A1 | 10/2001 | Murdock et al. |
| 2001/0036472 A1 | 11/2001 | Wong et al. |
| 2001/0048943 A1 | 12/2001 | Faour et al. |
| 2002/0006439 A1 | 1/2002 | Skluzacek et al. |
| 2002/0009487 A1 | 1/2002 | Murdock et al. |
| 2002/0035057 A1 | 3/2002 | Richter et al. |
| 2002/0035145 A1 | 3/2002 | Tsai et al. |
| 2002/0051807 A1 | 5/2002 | Faour et al. |
| 2002/0077361 A1 | 6/2002 | Peet et al. |
| 2002/0086870 A1 | 7/2002 | Radulovacki et al. |
| 2002/0099013 A1 | 7/2002 | Piccariello et al. |
| 2002/0111359 A1 | 8/2002 | Chang et al. |
| 2002/0147336 A1 | 10/2002 | Dow et al. |
| 2002/0155154 A1 | 10/2002 | Wong et al. |
| 2002/0156067 A1 | 10/2002 | Wong et al. |
| 2002/0156068 A1 | 10/2002 | Behan et al. |
| 2002/0161016 A1 | 10/2002 | Tam et al. |
| 2002/0192300 A1 | 12/2002 | Luo et al. |
| 2002/0193439 A1 | 12/2002 | Peet et al. |
| 2003/0013689 A1 | 1/2003 | Helton et al. |
| 2003/0017118 A1 | 1/2003 | Rabinowitz et al. |
| 2003/0027802 A1 | 2/2003 | Belanoff et al. |
| 2003/0027817 A1 | 2/2003 | Tollefson |
| 2003/0039680 A1 | 2/2003 | Dugger, III |
| 2003/0087803 A1 | 5/2003 | Yatvin et al. |
| 2003/0130266 A1 | 7/2003 | Radulovacki et al. |
| 2003/0139420 A1 | 7/2003 | Horseman |
| 2003/0175361 A1 | 9/2003 | Vaddadi |
| 2003/0185761 A1 | 10/2003 | Dugger, III |
| 2003/0211047 A1 | 11/2003 | Dugger, III |
| 2003/0219483 A1 | 11/2003 | Faour et al. |
| 2004/0062716 A1 | 4/2004 | Dugger, III |
| 2004/0073280 A1 | 4/2004 | Dae et al. |
| 2004/0099269 A1 | 5/2004 | Hale et al. |
| 2004/0116551 A1 | 6/2004 | Terry |
| 2004/0120895 A1 | 6/2004 | Dugger, III |
| 2004/0132797 A1 | 7/2004 | Lippa et al. |
| 2004/0138235 A1 | 7/2004 | Grzelak et al. |
| 2004/0142904 A1 | 7/2004 | Rariy et al. |
| 2004/0156791 A1 | 8/2004 | Rabinowitz et al. |
| 2004/0176595 A1 | 9/2004 | Dow et al. |
| 2004/0184997 A1 | 9/2004 | Rabinowitz et al. |
| 2004/0213816 A1 | 10/2004 | Weiner et al. |
| 2004/0224960 A1 | 11/2004 | Borchardt et al. |
| 2004/0242570 A1 | 12/2004 | Nudelman et al. |
| 2005/0074487 A1 | 4/2005 | Hsu et al. |
| 2005/0080087 A1 | 4/2005 | Pendri et al. |
| 2005/0181070 A1 | 8/2005 | Gadde et al. |
| 2005/0192268 A1 | 9/2005 | Ek et al. |
| 2005/0281752 A1 | 12/2005 | Dugger, III |
| 2005/0281753 A1 | 12/2005 | Dugger, III |
| 2006/0019901 A1 | 1/2006 | Shashoua |
| 2006/0034937 A1 | 2/2006 | Patel |
| 2006/0194784 A1 | 8/2006 | Ek et al. |
| 2006/0199798 A1 | 9/2006 | Ek et al. |
| 2006/0240050 A1 | 10/2006 | Surman et al. |
| 2006/0280692 A1 | 12/2006 | Rabinowitz et al. |
| 2006/0287323 A1 | 12/2006 | Ewing et al. |
| 2007/0059346 A1 | 3/2007 | Maibach |
| 2007/0072867 A1 | 3/2007 | Boyle et al. |
| 2007/0092586 A1 | 4/2007 | Cutler |
| 2007/0093471 A1 | 4/2007 | Cutler |
| 2007/0104778 A1 | 5/2007 | Zeng et al. |
| 2007/0129312 A1 | 6/2007 | Yatvin et al. |
| 2007/0161543 A1 | 7/2007 | Yu et al. |
| 2007/0190160 A1 | 8/2007 | Turos et al. |
| 2007/0197514 A1 | 8/2007 | Nudelman et al. |
| 2007/0207222 A1 | 9/2007 | Yu et al. |
| 2007/0225379 A1 | 9/2007 | Carrara et al. |
| 2007/0298999 A1 | 12/2007 | Wang |
| 2008/0026040 A1 | 1/2008 | Farr et al. |
| 2008/0026062 A1 | 1/2008 | Farr et al. |
| 2008/0039441 A1 | 2/2008 | Oberegger et al. |
| 2008/0108606 A1 | 5/2008 | Nudelman et al. |
| 2008/0124393 A1 | 5/2008 | Swanson et al. |
| 2008/0125669 A1 | 5/2008 | Suffin et al. |
| 2008/0146541 A1 | 6/2008 | Wu |
| 2008/0200508 A1 | 8/2008 | Rariy et al. |
| 2008/0287866 A1 | 11/2008 | Heller |
| 2008/0306025 A1 | 12/2008 | Yu et al. |
| 2008/0317853 A1 | 12/2008 | Kashid et al. |
| 2009/0124606 A1 | 5/2009 | Gacsalyi et al. |
| 2009/0233912 A1 | 9/2009 | Castile et al. |
| 2009/0252777 A1 | 10/2009 | Taft et al. |
| 2010/0016262 A1 | 1/2010 | Mehal et al. |
| 2010/0055133 A1 | 3/2010 | Duffield et al. |

FOREIGN PATENT DOCUMENTS

| | | |
|---|---|---|
| JP | 10175865 | 11/1996 |
| JP | 10-175865 * | 6/1998 |

FIGURE 1

STABLE CLOZAPINE SUSPENSION FORMULATION

TECHNICAL FIELD

The present invention is directed to a stable suspension formulation of clozapine for oral administration and to processes for preparing such formulations.

BACKGROUND TO THE INVENTION

Clozapine (8-chloro-11-(4-methyl-1-piperazinyl-5H-dibenzo[b,e][1,4]diazepine) is a well-known compound having anti-psychotic activity. Details about this compound are disclosed in monograph 2448 of the 13$^{th}$ edition of the Merck Index, the disclosure of which is hereby incorporated by way of reference.

Currently there are no liquid formulations of clozapine commercially available and, as a result, hospital pharmacists are often required to compound liquid formulations using crushed clozapine tablets for patients who have difficulty in swallowing or who feign ingestion.

Clozapine is insoluble in water and therefore the logical option for preparing a liquid formulation is to form it into an aqueous suspension. However, when clozapine is simply added directly to water, the compound settles rapidly to form a dense cake at the base of the aqueous mixture. The caking cannot easily be redistributed and as such would potentially compromise the accuracy of drug dose delivered to a patient.

In order to overcome this, a standard formulation technique would be to use a suitable wetting agent, to promote flocculation. Flocculation is a process where suspended particles agglomerate, forming larger particles that settle loosely and can be readily re-dispersed with gentle shaking thus overcoming the caking problem.

Clozapine is generally regarded as a stable molecule. But, surprisingly, when clozapine is formed into an aqueous suspension with a wetting agent and other formulating agents as might be considered standard in the art, the suspended active was found to be readily susceptible to hydrolysis which was indicated by a marked pH change on extended storage. As a result, the accuracy of the drug dose delivered to the patient could again be compromised.

There would be a clear advantage to be able to provide a physicochemically stable suspension formulation of clozapine for oral administration which would retain its physicochemical stability over a reasonable storage period. Such a product characteristic would be important to the production of a commercial liquid formulation.

SUMMARY OF THE INVENTION

In broad terms the invention in a first aspect may be seen to comprise a physicochemically stable aqueous composition including clozapine in suspension.

In broad terms, the invention may be seen to comprise a physicochemically stable aqueous composition including clozapine in suspension together with a wetting agent, wherein the pH of the composition is maintained in the range of about 6 to about 11.

Preferably, the pH is maintained within the desired range using a buffer system.

Preferably the buffer system is a sodium phosphate/sodium hydroxide buffer system.

Preferably the pH is maintained in the range of from about 6 to about 8.

Preferably the amount of clozapine in the composition is from about 0.1% to about 10% by weight based on the total volume of the composition.

Preferably the wetting agent is present in an amount of between about 0.1% and about 15%.

Preferably the wetting agent is selected from a suitable polyalcohol, such as propylene glycol, glycerin, or polyethylene glycol.

Preferably the composition includes polyvinyl pyrrolidone (PVP) as a crystal growth inhibitor.

Preferably the PVP is present in an amount of between about 0.1% and 2.0% by weight based on the total volume of the composition.

Preferably the composition includes a suspending agent and/or a preservative.

Preferably the suspending agent is present in an amount of between about 0.4% and about 2.0%.

Preferably the preservative is present in an amount of between about 0.1% and about 0.5%.

Preferably the suspending agent is xanthan gum.

Preferably the preservative is a mixture of methyl, propyl and butyl parabens.

Preferably the composition further includes a sweetening agent and/or a flavouring substance.

Preferably the composition includes: clozapine, glycerine, sodium dihydrogen phosphate dihydrate/NaOH buffer, xanthan gum, methyl paraben, propyl paraben, butyl paraben, and water.

Preferably the composition includes PVP.

Preferably the composition includes about:
(a) 50 mg/mL clozapine;
(b) 40 mg/mL propylene glycol;
(c) 7.8 mg/mL sodium dihydrogen phosphate dihydrate, q.s. sodium hydroxide;
(d) 6.0 mg/mL xanthan gum;
(e) 2.0 mg/mL methyl paraben;
(e) 0.5 mg/mL butyl paraben;
(g) 0.5 mg/mL chlorhexidine gluconate;
(h) q.s. water to final volume.

Preferably the composition includes about:
(a) 50 mg/mL clozapine;
(b) 108 mg/mL glycerine;
(c) 3.9 mg/mL sodium dihydrogen phosphate dihydrate, q.s. sodium hydroxide;
(d) 5.2 mg/mL xanthan gum;
(e) 2.2 mg/mL methyl paraben;
(e) 0.2 mg/mL propyl paraben;
(g) 0.2 mg/mL butyl paraben;
(h) 10.8 mg/mL PVP
(i) 86.4 mg/mL sucrose
(j) q.s. water to final volume.

In a further aspect, the invention may be seen to comprise a method for preparing a physicochemically stable aqueous formulation including clozapine in suspension including the step of controlling the pH of the formulation between about 6 and about 11.

In a further aspect, the invention may be seen to comprise a method for producing a physicochemically stable aqueous composition including clozapine in suspension including the following steps:
(a) stirring the active ingredient clozapine with about three quarters of the propylene glycol ascribed to the batch;
(b) addition of the buffer salt (and optionally sweetening agents) dissolved in about half the volume of water ascribed to the batch with constant stirring;
(c) adjusting the pH value with the base component of the buffer with mixing;

(d) addition of the preservatives dissolved in the remaining propylene glycol;
(e) slow addition of the suspending agent with continuous stirring until the mixture thickens;
(f) further diluting the suspension with water to the desired end-volume.

In a further aspect, the invention may be seen to comprise a method for producing a physicochemically stable aqueous composition including clozapine in suspension including the following steps:
(a) stirring the active ingredient clozapine with about three quarters of the glycerine ascribed to the batch;
(b) addition of the buffer salt (and optionally sweetening agents) dissolved in about half the volume of water ascribed to the batch with constant stirring;
(c) adjusting the pH value with the base component of the buffer with mixing;
(d) addition of the preservatives dissolved in a small volume of water;
(e) slow addition of the suspending agent wetted with the remaining glycerine with continuous stirring until the mixture thickens;
(f) further diluting the suspension with water to the desired end-volume.

Preferably the method includes the step of PVP addition.

Preferably the PVP is added as an aqueous solution following addition of the suspending agent.

DETAILED DESCRIPTION

The present invention is broadly concerned with the preparation of a physicochemically stable aqueous composition including clozapine in suspension formulation of clozapine for oral administration.

Clozapine is generally regarded as a stable molecule which is practically insoluble in water. On addition of clozapine directly to water, the drug settles to form a dense cake at the base of the mixture which cannot be readily redistributed. When a wetting agent was used, the caking problem was overcome but it was surprisingly found that the active was readily susceptible to hydrolysis. As a result, the clozapine suspension was not suitable for commercial use as it could not be stored for a reasonable period to allow later, accurate, use.

Unexpectedly, it has been found that it is possible to impart considerable stability to an aqueous suspension of clozapine if the pH of the aqueous suspension is controlled and maintained at a level between about 6 and about 11. Preferably the pH will be maintained within the range of 6 to 9 and more preferably between 7 and 8. If the pH is not controlled and maintained within this range, the active degrades quite quickly.

Once this is recognised the creation of a composition having a physicochemical stability suitable for developing a commercially viable aqueous suspension can be achieved.

In order to control the pH, a suitable buffer system should be used. Buffer systems comprise mixtures of appropriate amounts of conjugate bases of various organic acids adjusted to the desired pH value with NaOH or HCl. Examples of suitable bases include but are not limited to: sodium citrate, potassium citrate, sodium bicarbonate, potassium bicarbonate, sodium dihydrogen phosphate and potassium dihydrogen phosphate. The buffer should have sufficient capacity to remain in the desired pH range throughout the product shelf life. Such issues would be well known to the skilled person.

The preferred buffer system is sodium dihydrogen phosphate/sodium hydroxide where the phosphate concentration ranges from about 10 mM to about 200 mM, preferably 10mM to 50 mM. Below about 10 mM there is insufficient capacity to control the pH on prolonged storage, while phosphate concentrations above about 200 mM have been found to promote recrystallisation of the drug substance.

The amount (w/v) of clozapine in the composition will be a suitable amount as will be known to the skilled person in the art. Ranges between 0.1% to 10%, preferably from 2.5% to 7.5% in particular 5% (50 mg/mL) would be used. As will be known to the skilled person, simple dilution of the suspension could be used to deliver a required dosage amount to a patient as needed.

The composition will also preferably include a wetting agent selected from any one or more of propylene glycol, glycerin or polyethylene glycol and like compounds as would be known to the skilled person. The % range of wetting agent in the composition will preferably be between about 0.1% and 20%, more preferably between 1% and 15%.

The oral suspension according to the present invention will preferably also include a preservative to prevent the growth of micro-organisms such as bacteria, yeasts and fungi. The preservative should also be physicochemically stable in the pH range of 6 to 11, preferably 6 to 9. Suitable preservatives could be selected from any one or more of: chlorhexidine; methyl paraben; propyl paraben; butyl paraben and their salts; diazolidinyl urea (Germall II.RTM); quaternary compounds, eg benzalkonium chloride and cetylpyridinium chloride, phenyl ethyl alcohol and the like. The concentration of preservatives may range from about 0.01% to about 0.5%.

When preparing a formulation with the active suspended in an aqueous carrier it is often necessary to add a suspending/stabilizing agent or agents to prevent settling of the active material. Over time the settling (even if ordinarily capable of redistribution) could lead to caking of the active to the inside walls of the product pack, leading to difficulties with redispersion and accurate dispensing. Suitable stabilising agents are the polysaccharide stabilisers such as xanthan, guar and tragacanth gums as well as the cellulose derivatives HPMC (hydroxypropyl methylcellulose) and Avicel RC-591 (microcrystalline cellulose/ sodium carboxymethyl cellulose). While Carbopol.RTM (carboxyvinyl polymer) is also a stabilising agent of use in the formulating art, research has shown that when this is used in the present formulation a physicochemically stable composition is not achieved. Polyvinylpyrrolidone (PVP) can also be referred to as a stabilising agent but, in this context, has been found to be more correctly referred to as a crystal growth inhibitor due to its particular effect in this regard.

In preferred compositions both PVP and another stabilising agent (eg xanthan gum) will be present.

The composition will preferably include polyvinylpyrrolidone (PVP) as a crystal growth inhibitor. Preferably the PVP will be present in an amount of between 0.5% and 2.0%. Inclusion of the PVP imparts a surprising level of additional physicochemical stability to the composition and is thus a most preferred option for preparing a commercially viable composition.

A variety of sweeteners and flavourings could also be added as desired and as known to the skilled person. Additives such as sucrose and/or banana flavouring, for example, could be added. Sucrose could be replaced by xylitol or sorbitol for example when the composition is for use with diabetics.

Compositions according to the present invention have been characterised by their improved physicochemical stability. The term "physicochemically stable", or similar terms, refer to an aqueous suspension formulation wherein, after storage for a period of up to about three months at a temperature of 40° C., the residual amount of clozapine is 95% or more of the initial clozapine concentration.

The term clozapine as used herein, refers to the free base form and pharmaceutically acceptable acid addition salts thereof. Possible salts include, but are not limited to, inorganic salts such as phosphates, carbonates and organic salts such as citrate and acetate. The term addition salt also includes the solvates of clozapine including, but not limited to, hydrates and alcoholates.

The aqueous suspensions according to the present invention are well suited to dilution with acidic non-alcoholic beverages such as citrus drinks, soft-drinks and the like. This option aids the palatability of the liquid and may result in improved patient compliance. As stated earlier, the dilution requirements to achieve an effective clozapine dosage would be well within the knowledge of the skilled person in this particular art.

Preferred forms of the composition will include:
(a) clozapine;
(b) a solvent (eg water)
(c) a wetting agent to disperse the clozapine;
(d) a stabilizing agent;
(e) a buffer; and preferably
(f) PVP.

A particular oral composition according to the present invention will include:
(a) clozapine;
(b) a suitable wetting agent to disperse the drug substance;
(c) a suitable buffer to control the pH in the range of 6 to 9;
(d) a stabilizing agent;
(e) a preservative;
(f) water; and preferably
(g) PVP.

Preferably the clozapine would be present in an amount of between about 0.1% and 10%; the stabilising agent between about 0.5% and 2%; and the preservative between about 0.1% and 0.5%.

A more preferred oral composition according to the present invention includes:
(a) 5.0% clozapine;
(b) 4.0% propylene glycol
(c) 0.78% sodium dihydrogen phosphate dihydrate and sufficient sodium hydroxide to adjust the pH range from 6 to 9;
(d) 8.0% sucrose;
(e) 0.60% xanthan gum;
(e) 0.2% methyl paraben;
(g) 0.05% butyl paraben;
(h) 0.05% chlorhexidine gluconate
(i) optionally 1.0% PVP;
(j) water q.s to 100%.

In particular, the process to produce the composition may include the following steps:
(a) stirring the active ingredient clozapine with about three quarters of the propylene glycol ascribed to the batch;
(b) addition of the buffer salt (and optionally sweetening agents) dissolved in about half the volume of water ascribed to the batch with constant stirring;
(c) adjusting the pH value with the base component of the buffer with mixing;
(d) addition of the preservatives dissolved in the remaining propylene glycol;
(e) slow addition of the suspending agent with continuous stirring until the mixture thickens;
(f) optional addition of PVP dissolved in a portion of the remaining water ascribed to the batch with constant stirring;
(g) further diluting the suspension with water to the desired end-volume.

The NaOH concentration used for adjustment of pH is preferably 4.6 M.

Another preferred oral composition according to the invention includes:
(a) 50.0 mg/mL clozapine;
(b) 108.0 mg/mL glycerine
(c) 4.2 mg/mL sodium dihydrogen phosphate dihydrate and sufficient sodium hydroxide to adjust the pH range from 6 to 9;
(d) 86.4 mg/mL sucrose;
(e) 5.2 mg/mL xanthan gum;
(f) 2.2 mg/mL methyl paraben;
(g) 0.2 mg/mL propyl paraben
(h) 0.2 mg/mL butyl paraben
(i) optionally 10.8 mg/mL PVP;
(j) water q.s to 100% (approx. 813 mg/mL).

The NaOH concentration used for adjustment of pH is preferably 0.1 M.

In particular, the process may comprise the following steps:
(a) stirring the active ingredient clozapine with about three quarters of the glycerine ascribed to the batch;
(b) addition of the buffer salt (and optionally sweetening agents) dissolved in about half the volume of water ascribed to the batch with constant stirring;
(c) adjusting the pH value with the base component of the buffer with mixing;
(d) addition of the preservatives dissolved in a small volume of water;
(e) slow addition of the suspending agent wetted with the remaining glycerine with continuous stirring until the mixture thickens;
(f) optional addition of PVP dissolved in a portion of the remaining water ascribed to the batch with constant stirring;
(g) further diluting the suspension with water to the desired end-volume.

EXAMPLES

The following examples are intended to illustrate the scope of the present invention in all its aspects but not to limit it thereto.

Example 1

| F1: Oral Suspension (pH = 7.0) | |
|---|---|
| Ingredient | Quantity (mg) |
| Clozapine | 50 |
| Propylene Glycol (I) | 30 |
| Sodium Dihydrogen Phosphate Dihydrate | 7.8 |
| Sodium hydroxide | q.s ad pH = 7.0 |

| F1: Oral Suspension (pH = 7.0) | |
| --- | --- |
| Ingredient | Quantity (mg) |
| Sucrose | 80 |
| Xanthan Gum | 6.0 |
| Propylene Glycol (II) | 10 |
| Methyl Paraben | 2.0 |
| Butyl Paraben | 0.5 |
| Chlorhexidine Gluconate | 0.5 |
| Water | q.s ad 1 mL |

(1) Clozapine (50 mg) was mixed into a paste with Propylene Glycol (30 mg).

(2) Sodium Dihydrogen Phosphate Dihydrate (7.8 mg as a 1 M solution) was added to Fraction (1) with stirring.

(3) Sucrose (80 mg), dissolved in 0.35 mL of water was added to Fraction (2) with stirring.

(4) NaOH (4.6 mol/L) was added to Fraction (3) to adjust the pH to about 7.0.

(5) Methyl Paraben (2 mg) and Butyl Paraben (0.5 mg) were dissolved in Propylene Glycol (10 mg) with gentle warming.

(6) Fraction (5) was added slowly to Fraction (4) with constant stirring.

(7) Chlorhexidine Gluconate (0.5 mg) was dissolved in 0.2 mL of water.

(8) Fraction (7) was added to Fraction (6) with constant stirring.

(9) Xanthan Gum (6.0 mg) was slowly added to Fraction (8) with constant stirring taking care not to aerate the suspension.

(10) Fraction (9) was further diluted with water to 1 mL.

In a similar way there were prepared:

| F2: Oral Suspension (pH = 6.0 ± 0.1) | |
| --- | --- |
| Ingredient | Quantity (mg) |
| Clozapine | 50 |
| Potassium Dihydrogen Phosphate Dihydrate | 27.2 |
| NaOH | q.s. ad pH = 6.0 |
| Sucrose | 80 |
| Xanthan Gum | 5.0 |
| Potassium Sorbate | 2.0 |
| Water | q.s. ad 1 mL |

| F3: Oral Suspension (pH = 7.0 ± 0.1) | |
| --- | --- |
| Ingredient | Quantity (mg) |
| Clozapine | 50 |
| Potassium Dihydrogen Phosphate Dihydrate | 27.2 |
| NaOH | q.s. ad pH = 7.0 |
| Sucrose | 80 |
| Xanthan Gum | 5.0 |
| Potassium Sorbate | 2.0 |
| Water | q.s. ad 1 mL |

| F4: Oral Suspension (pH = 8.0 ± 0.1) | |
| --- | --- |
| Ingredient | Quantity (mg) |
| Clozapine | 50 |
| Potassium Dihydrogen Phosphate Dihydrate | 27.2 |
| NaOH | q.s. ad pH = 8.0 |
| Sucrose | 80 |
| Xanthan Gum | 5.0 |
| Potassium Sorbate | 2.0 |
| Water | q.s. ad 1 mL |

Example 2

The Table below summarizes the clozapine concentrations for formulations F1-F4 of Example 1 measured after a particular storage time of the composition at a particular temperature, expressed as the percentage of the initial clozapine concentration.

| | Formulation | | | |
| --- | --- | --- | --- | --- |
| | F1 | F2 | F3 | F4 |
| 1 month @ 5° C. | 102.3 | 102.6 | 101.0 | 100.2 |
| 1 month @ 50° C. | 98.4 | 100.6 | 101.1 | 102.7 |
| 3 month @ 40° C. | omitted | 104.7 | omitted | 97.8 |

Example 3

| 25 mg/ml Clozapine Suspension pH 6.0 | |
| --- | --- |
| Ingredients | mg |
| Sucrose | 80.0 |
| Methyl paraben | 0.5 |
| Propyl paraben | 0.1 |
| Clozapine | 25.0 |
| Hydroxypropylmethyl cellulose (HPMC) | 10.0 |
| Potassium dihydrogen phosphate | 24.0 |
| Water | 910.0 |

1. Dissolve the potassium dihydrogen phosphate in 910 mg of water and adjust the pH to 6.0.

2. Heat ⅓ of the phosphate buffer solution to 70° C., add methyl paraben and propyl paraben and dissolve.

3. Add with rapid stirring HPMC and mix for 2 minutes.

4. Add another ⅓ of the phosphate buffer solution and rapidly decrease the temperature of the mixture to room temperature continuing to stir for a further 15 minutes.

5. Add the remaining ingredients and continue to mix for a further 30 minutes.

| Results | | | |
| --- | --- | --- | --- |
| Conditions | Description | Assay (mg/ml) | % Yield |
| Time Zero | A yellow suspension | 25.0 based on compounding | 100.0 |

-continued

Results

| Conditions | Description | Assay (mg/ml) | % Yield |
|---|---|---|---|
| 14 m/25° C./60% RH (RD4758) | A yellow suspension and settlement observed but easily re-dispersed after shaking | 27.0 | 108.0 |
| 14 m/40° C. (RD4775) | A yellow suspension and settlement observed but easily re-dispersed after shaking | 25.4 | 101.6 |

Example 4

25 mg/ml Clozapine Suspension pH 8.0

| Ingredients | mg |
|---|---|
| Microcrystalline cellulose/sodium carboxymethyl cellulose (Avicel RC 591) | 12.0 |
| Hydroxypropylmethyl cellulose (HPMC) | 10.0 |
| Tween 80 | 5.0 |
| Clozapine | 25.0 |
| Methyl paraben | 0.5 |
| Propyl paraben | 0.1 |
| Sucrose | 80.0 |
| Potassium dihydrogen phosphate | 23.4 |
| Water | 884.0 |

1. Dissolve the potassium dihydrogen phosphate in 884 mg of water and adjust the pH to 8.0.
2. Heat ⅓ of the phosphate buffer solution to 70° C., add methyl paraben, propyl paraben and Tween 80 and dissolve.
3. Add with rapid stirring HPMC and mix for 2 minutes.
4. Add another ⅓ of the phosphate buffer solution and rapidly decrease the temperature of the mixture to room temperature continuing to stir for a further 15 minutes.
5. Slowly add Avicel RC 591 and continue stirring until visually smooth.
6. Add the remaining ingredients and continue to mix for a further 30 minutes.

Results

| Conditions | Description | Assay (mg/ml) | % Yield |
|---|---|---|---|
| Time Zero | A yellow suspension | 24.5 | 100.0 |
| 14 m/25° C./60% RH (RD4759) | A yellow suspension and settlement observed but easily re-dispersed after shaking | 26.7 | 109.0 |
| 14 m/40° C. (RD4776) | A yellow suspension and settlement observed but easily re-dispersed after shaking | 28.2 | 115.1 |

Results—Examples 3 and 4

The formulations of Examples 3 and 4 were stored at 40° C. and 25° C./60% RH for ~14 months. The suspending agent in Example 3 was Metolose (HPMC). The suspending agent in Example 4 was a combination of Metolose (HPMC) and Avicel RC591. Both formulations did not show crystal growth at these pHs. Both formulations settle fairly quickly but were easily re-dispersed after shaking. The Clozapine assay results for both formulations show no degradation after 14 months and are thus defined as being physicochemically stable.

The formulation of Example 4 at pH 6 & 7 produced yellow crystals while stored at 25° C./60% RH and 40° C. for ~14 months and are thus defined as being chemically unstable at this pH. Inclusion of PVP (crystal growth inhibitor) would be an option to correct this instability. However, the formulation of Example 4 at pH 8 and the formulation of Example 3 at pH 6 were shown to be physicochemically stable after ~14 months at 40° C. and 25° C./60% RH.

Example 5

Alternatives to sucrose (xylitol, sorbitol) in 50 mg/ml Clozapine formulations

| Ingredients | Formulation (mg/ml) | |
|---|---|---|
| | Xylitol | Sorbitol |
| Xylitol | 86.4 | — |
| Sorbitol | — | 86.4 |
| PVP | 10.8 | 10.8 |
| Clozapine | 50.0 | 50.0 |
| Sodium Dihydrogen Phosphate dihydrate | 4.2 | 4.2 |
| Methyl Paraben (Na) | 2.2 | 2.2 |
| Propyl Paraben (Na) | 0.2 | 0.2 |
| Butyl Paraben (Na) | 0.2 | 0.2 |
| Xanthan gum | 5.2 | 5.2 |
| Glycerine | 140.4 | 140.4 |
| Water | 780.3 | 780.3 |
| Sodium Hydroxide | 0.1 | 0.1 |

1. Mix into a paste the Clozapine with ¾ of the glycerine.
2. Dissolve Sodium Dihydrogen Phosphate Dihydrate in 3% of the required water and add to Fraction (1) with stirring.
3. Dissolve the sorbitol or xylitol and the three parabens in about 50% of the required water and add to Fraction (2) with stirring.
4. Add NaOH (1 mol/L) to Fraction (3) to adjust the pH to about 7.0. Add another 30% of the required water with stirring.
5. Wet the xanthan gum with ½ of the remaining glycerine. Add to Fraction (4) with stirring, rinsing the container with the remaining glyerine.
6. Dissolve the PVP with 5% of the required water and add to Fraction (5) with constant stirring.
7. Add the remaining water and continue to mix until the gum is well hydrated.

Results: 3 months stability at 40° C./75% RH (Results in ( ) are % of initial result).

| Description | | pH | Assay mg/ml (% of initial result) |
|---|---|---|---|
| Xylitol | Slight flocculant settlement but readily re-disperses to a yellow suspension. | 6.98 | (101.7%) |
| Sorbitol | Slight flocculant settlement but readily re-disperses to a yellow suspension. | 6.98 | (99.8%) |

Use of Xylitol or Sorbitol in place of sucrose would have advantages in the treatment of patients who are also diabetic.

As shown in the above Example, formulations according to the invention that include xylitol or sorbitol in place of sucrose show acceptable stability characteristics.

Example 6

| 50 mg/ml Clozapine formulation. Trial formulation 42 | |
|---|---|
| Ingredients | Amount (mg/ml) |
| Sucrose | 86.4 |
| PVP | 10.8 |
| Clozapine | 50.0 |
| Sodium Dihydrogen Phosphate dihydrate | 4.2 |
| Methyl Paraben (Na salt) | 2.2 |
| Propyl Paraben (Na salt) | 0.2 |
| Butyl Paraben (Na salt) | 0.2 |
| Xanthan gum | 5.2 |
| Glycerine | 108.0 |
| Water | 811.6 |
| Banana Flavour canary | 1.1 |
| Sodium Hydroxide | 0.1 |

1. Mix into a paste the Clozapine with the glycerine.
2. Dissolve Sodium Dihydrogen Phosphate Dihydrate in 3% of the required water and add to Fraction (1) with stirring.
3. Dissolve the sucrose and the three parabens in about 50% of the required water and add to Fraction (2) with stirring.
4. Add NaOH (1 mol/L) to Fraction (3) to adjust the pH to about 7.0. Add another 30% of the required water with stirring.
5. With rapid stirring add the xanthan gum to Fraction (4).
6. Dissolve the PVP with 5% of the required water and add to Fraction (5) with constant stirring.
7. Add the remaining water and continue to mix until the gum is well hydrated.

Tables 1 and 2 below show the pharmacokinetic results obtained in a pilot scale bioequivalence Study of Trial Formulation 42 against a standard Clozapine tablet. It is considered that based on these data, when the usual number of subjects are used, the suspension will be shown to be bioequivalent to the tablet for the following reasons:
1. The absolute values of the mean AUC(0-inf) test and AUC (0-inf) reference are such that the ratio of AUC(0-inf) test/ AUC(0-inf) is 91%. In the applicant's experience, if the ratio is >85% with six subjects then the study will pass when a statistically significant number of subjects is used.
2. The absolute values of the mean Cmax test and Cmax reference are such that the ratio of Cmax test/Cmax reference is 86%. In the applicant's experience if the ratio is >80% with six subjects then the study will pass when a statistically significant number of subjects is used.
3. It is thought that one cause of the mean ratios being <100% may be due to aeration of the suspension during preparation of the syringes for oral administration such that slightly less than 0.25 mL was administered. Processes for ensuring aeration of the suspension is kept to a minimum will be incorporated into syringe preparation in the larger studies.
4. The 90% Cl for LogAUC(0-inf) has been determined to be 0.777-1.005. In the applicant's experience if the 90% Cl is in the range 0.70-1.30 for six subjects then the study will pass when a statistically significant number of subjects is used.
5. The 90% Cl for LogCmax has been determined to be 0.754-1.032. In the applicant's experience if the 90% Cl is in the range 0.70-1.40 for six subjects then the study will pass when a statistically significant number of subjects is used. In fact the 90% Cl for LogCmax at 0.754-1.032 is already in compliance with the wider interval of 0.75-1.33 allowed by the Note for Guidance on the Investigation of Bioequivalence and Bioavailability CPMP/EWP/QWP/1401/98. This Note is accepted as the guidance to be followed when conducting bioequivalence trials in either New Zealand or Australia.

TABLE 1

Summary of Pharmacokinetic Results Obtained - Formulation of Example 6

| | $AUC_{0-\infty}$ (ng · hr/ml) Mean S.D Range | $AUC_{0-t}$ (ng · hr/ml) Mean S.D Range | Cmax (ng/ml) Mean S.D Range | Tmax (hr) Mean S.D Range | t½ (hr) Mean S.D Range |
|---|---|---|---|---|---|
| Clozapine 50 mg/ml suspension (T) 0.25 mL B: Trial 42 (Douglas, New Zealand) | 260.75 117.08 (112.50-448.72) | 250.31 114.48 (105.88-438.95) | 28.78 10.40 (16.80-46.90) | 1.42 0.20 (1.00-1.52) | 15.80 4.27 (8.85-20.65) |
| Clozapine 25 mg tablets (R) ½ tablet B: 001G8380T (Novartis, USA) | 286.64 99.49 (142.64-390.13) | 275.52 94.33 (139.96-373.34) | 33.62 14.13 (15.40-55.90) | 1.83 1.58 (0.98-5.02) | 15.15 4.15 (8.67-20.77) |
| Mean Ratio[1] | 90.97 | 90.85 | 85.62 | 77.27 | 104.30 |
| Geometric Ratio[1] | 88.39 | 87.85 | 88.21 | 93.87 | — |

[1]Mean Ratio = Mean (T)/Mean (R)

TABLE 2

Clozapine Bioequivalence Summary Statistics for the Example 6 Formulation and Clozapine Tablets

| Variable | Anova | 90% C.I. |
|---|---|---|
| $Log_{10}$ ($AUC_0$-∞) | 0.111 | (0.777, 1.005)* |
| $Log_{10}$ (AUC0-t) | 0.094 | (0.774, 0.997) |
| $Log_{10}$ (Cmax) | 0.164 | (0.754, 1.032)* |
| $AUC_0$-∞ | 0.254 | (0.765, 1.054) |
| AUC0-t | 0.242 | (0.766, 1.051) |
| Cmax | 0.103 | (0.711, 1.002) |
| Tmax | 0.518 | (0.089, 1.457) |

TABLE 2-continued

Clozapine Bioequivalence Summary Statistics for the Example 6 Formulation and Clozapine Tablets

| Variable | Anova | 90% C.I. |
|---|---|---|
| Tmax[+] | Significant difference | (0.547, 1.513) |
| t½ | 0.423 | (0.909, 1.177) |

Figure 1:
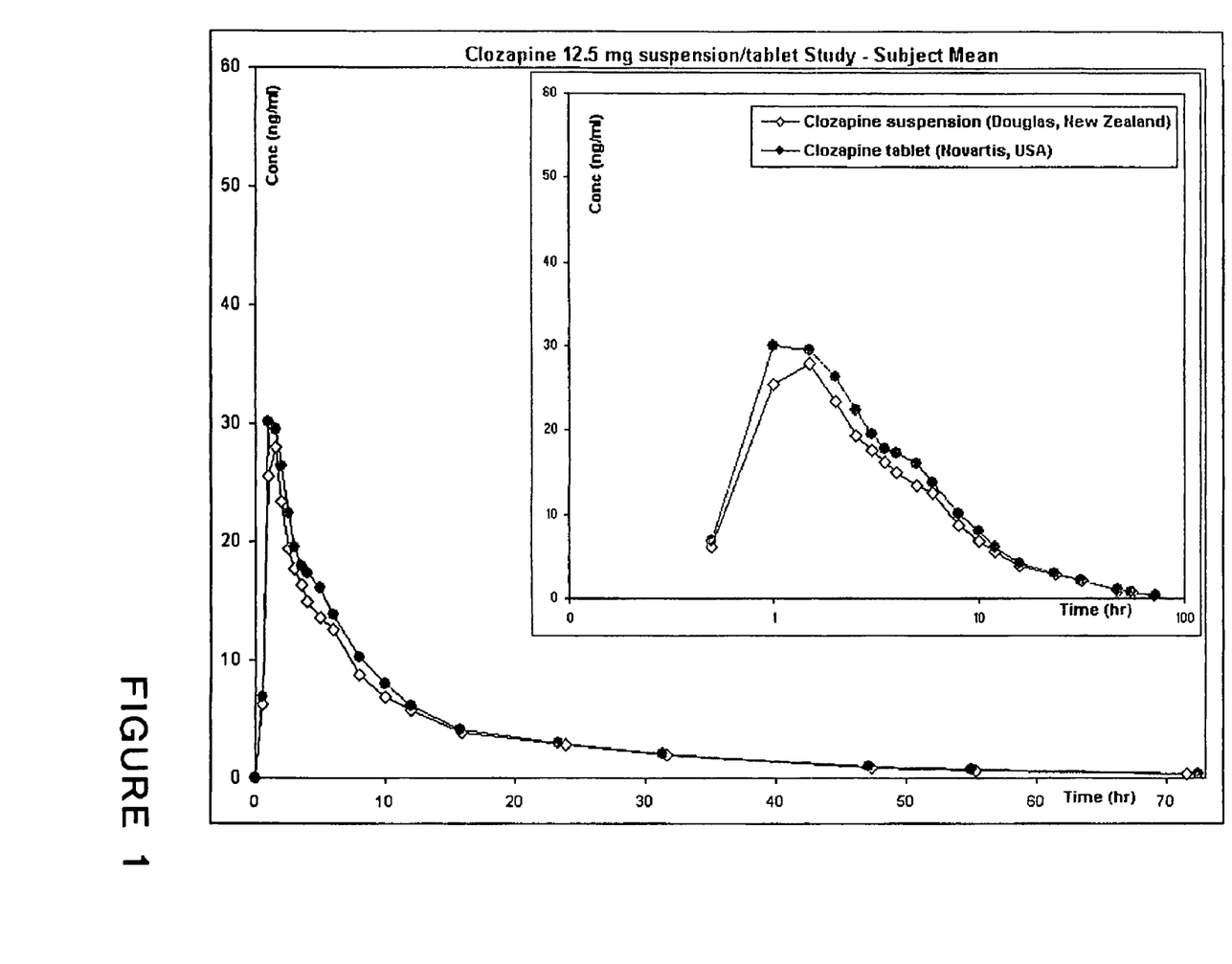
FIG. 1 shows the mean plasma concentration (ng/ml) versus time (hrs) of clozapine following the oral administration of 0.25 mg/ml suspension according to a preferred form of the invention and half a 25 mg Clozapine tablet at time zero.

*Criteria used to assess Bioequivalence, ie 90% CI between 0.80 and 1.25 for $AUC_{0-\infty}$ and Cmax
[+]Nonparametic Analysis Tabulated data showing the mean plasma concentration versus time of Trial Formulation 42 (Example 6) and a Clozapine tablet are detailed in FIG. 1.

Example 7 Clozapine Suspension Stability Over PH Range

Method of Preparation of Clozapine Formulations used in Table 3 below:

1. Clozapine (20 g) was combined with 50 g of a phosphate buffer I (pH 3) or phosphate buffer II (pH 5, 6, 7, 11)
2. A further 350 g of phosphate buffer I (pH 3) or phosphate buffer II (pH=5, 6, 7, 11) was then added to the mixture from 1
3. The pH of the mixture from 2 was adjusted to the desired value by the addition of concentrated phosphoric acid or sodium hydroxide as appropriate.
4. Additional buffer was added to the mixture from 3 to a final mass of 400 g (5% w/w clozapine)

Preparation of the buffer solutions was as follows:

Phosphate Buffer I 3.4 g of potassium dihydrogen phosphate was dissolved in 900 mL of water. The pH was adjusted to 3.0 with phosphoric acid and the resulting solution diluted to 1000 mL Phosphate Buffer II 18.72 g of sodium dihydrogen phosphate was dissolved in water and made to a final volume of 2 L.

Table 3 below shows stability data for aqueous suspensions of clozapine at a range of pH values.

TABLE 3

| | pH 3 | | pH 5 | | pH 6 | |
|---|---|---|---|---|---|---|
| | Initial Testing | 5 days/ 70° C. Storage | Initial Testing | 5 days/ 70° C. Storage | Initial Testing | 5 days/ 70° C. Storage |
| Description | Yellow powder in yellow solution | Orange powder in red solution | Yellow powder in yellow solution | Yellow powder in dark yellow solution | Yellow powder in yellow solution | Yellow powder in yellow solution |
| pH | 3.01 | 3.86 | 5.20 | 5.70 | 5.99 | 6.20 |
| Total Unknown Impurities % | 0.18 | 4.14 | 0.00 | 0.07 | 0.00 | 0.04 |
| Impurity A (CDD) % | 0.10 | 36.70 | 0.00 | 0.80 | 0.00 | 0.52 |
| Total impurities % | 0.28 | 40.84 | 0.00 | 0.87 | 0.00 | 0.56 |

| | pH 7 | | pH 11 | |
|---|---|---|---|---|
| | Initial Testing | 5 days/ 70° C. Storage | Initial Testing | 5 days/ 70° C. Storage |
| Description | Yellow powder in yellow solution | Yellow powder in yellow solution | Yellow powder in light yellow coloured solution | Yellow powder in light yellow coloured solution |
| pH | 6.95 | 6.54 | 11.08 | 10.54 |
| Total Unknown Impurities % | 0.00 | 0.00 | 0.00 | 0.00 |
| (Impurity A (CDD) % | 0.00 | 0.10 | 0.00 | 0.00 |
| Total impurities % | 0.00 | 0.10 | 0.00 | 0.00 |

Results at 70° C. after 5 days indicate that the clozapine molecule is very stable when the pH is controlled between pH 6 and pH 11. At pH 3 clozapine degrades rapidly, with degradants present at a level of about 41%, after 5 days at 70° C. At pH 5 the level of growth impurity A (CDD "8-chloro-5H-Dibenzo-[b,e]-1,4-Diazepine-11-one) is unacceptably high.

Administration of the Suspension

It is envisaged that the product would be supplied in a glass or plastic container with a child proof closure together with a syringe marked in mL for ease of dosing. The minimum marked volume of the syringe would be 0.25 mL to allow for accurate dosing of the recommended starting dose of 12.5 mg based on the Clozapine 50 mg/mL product. The maximum volume of the syringe would be around 10 mL to allow ready dispensing of the range of most therapeutic doses in one application. The syringe should be emptied into a non-alcoholic drink with stirring. Orange juice, coffee and some carbonated soft drinks are suitable. The syringe should be rinsed and dried after use.

The foregoing describes the invention including preferred forms thereof, alterations or modifications as would be obvious to a person skilled in this particular art are intended to be included within the scope of the invention as defined in the attached claims.

The invention claimed is:

1. A physicochemically stable aqueous composition for oral administration comprising:
    clozapine in suspension;
    a wetting agent selected from any one or more of propylene glycol, glycerin, or polyethylene glycol;
    a stabilizing agent selected from anyone or more of xanthan gum, guar gum, tragacanth gum, hydroxypropyl methylcellulose, or microcrystalline cellulose; and
    a buffer, wherein the pH of the composition is maintained within the range of about 6 to about 11.

2. The composition according to claim 1 wherein the buffer is a sodium phosphate/sodium hydroxide buffer.

3. The composition according to claim 1 wherein the pH is maintained in the range of from about 6 to about 8.

4. The composition according to claim 1 wherein the amount of clozapine in the composition is from about 0.1% to about 10% by weight based on the total volume of the composition.

5. The composition according to claim 1 comprising a wetting agent in an amount of between about 0.1% and about 15%.

6. The composition according to claim 1 further comprising a suspending agent and/or a preservative.

7. The further comprising according to claim 1 comprising a preservative selected from any one or more of methyl, propyl and butyl parabens.

8. The composition according to claim 1 wherein the composition includes: clozapine, glycerine, sodium dihydrogen phosphate dihydrate/NaOH buffer, xanthan gum, methyl paraben, propyl paraben, and water.

9. A method for preparing a physicochemically stable aqueous composition including clozapine in suspension according to claim 1, the method comprising the step of controlling the pH of the formulation between about 6 and about 11.

10. The method according to claim 9 wherein the pH is controlled between 6 and 8.

11. The method according to claim 9 wherein the method further includes the addition of polyvinyl pyrrolidone.

12. A method of producing a physicochemically stable aqueous composition comprising clozapine in suspension according to claim 1 comprising the following steps:
    (a) stirring the clozapine with about three quarters of propylene glycol ascribed to the batch;
    (b) addition of the buffer salt (and optionally sweetening agents) dissolved in about half the volume of water ascribed to the batch with constant stirring;
    (c) adjusting the pH value with the base component of the buffer with mixing;
    (d) addition of the preservatives dissolved in the remaining propylene glycol;
    (e) slow addition of the suspending agent with continuous stirring until the mixture thickens; and,
    (f) further diluting the suspension with water to the desired end-volume.

13. A method for producing a physicochemically stable aqueous composition comprising clozapine in suspension according to claim 1 comprising the following steps:
    (a) stirring the clozapine with about three quarters of glycerine ascribed to the batch;
    (b) addition of the buffer salt (and optionally sweetening agents) dissolved in about half the volume of water ascribed to the batch with constant stirring;
    (c) adjusting the pH value with the base component of the buffer with mixing;
    (d) addition of the preservatives dissolved in a small volume of water;
    (e) slow addition of the suspending agent wetted with the remaining glycerine with continuous stirring until the mixture thickens; and,
    (f) further diluting the suspension with water to the desired end-volume.

14. The method according to claim 12 wherein polyvinyl pyrrolidone is added as an aqueous solution following addition of the suspending agent.

15. The method according to claim 13 wherein polyvinyl pyrrolidone is added as an aqueous solution following addition of the suspending agent.

16. The composition according to claim 1 wherein the composition further includes a sweetening agent and/or a flavoring substance.

17. The composition according to claim 1 wherein the composition comprises: clozapine, glycerin, sodium dihydrogen phosphate dihydrate/NaOH buffer, xanthan gum, sodium methyl paraben, sodium propyl paraben and water.

18. The composition according to claim 1 wherein the composition is stable for at least 14 months.

19. A physicochemically stable aqueous composition for oral administration comprising:
    clozapine in suspension;
    a wetting agent selected from any one or more of propylene glycol, glycerin, or polyethylene glycol;
    polyvinyl pyrrolidone; and
    a buffer, wherein the pH of the composition is maintained within the range of about 6 to about 11.

* * * * *